(12) United States Patent
Yoon

(10) Patent No.: US 6,224,614 B1
(45) Date of Patent: May 1, 2001

(54) SUTURING INSTRUMENT WITH ANGLED NEEDLE HOLDER AND METHOD FOR USE THEREOF

(76) Inventor: InBae Yoon, 11886 Farkside Rd., Ellicott City, MD (US) 21042

( * ) Notice: Subject to any disclaimer, the term of this patent is extended or adjusted under 35 U.S.C. 154(b) by 0 days.

(21) Appl. No.: 09/334,634

(22) Filed: Jun. 17, 1999

Related U.S. Application Data

(60) Provisional application No. 60/089,659, filed on Jun. 17, 1998.

(51) Int. Cl.[7] .................................................... A61B 17/04
(52) U.S. Cl. ............................................................ 606/147
(58) Field of Search ................................... 606/141, 139, 606/144, 145, 147, 148, 149

(56) References Cited

U.S. PATENT DOCUMENTS

| | | | |
|---|---|---|---|
| 5,234,443 | * | 8/1993 | Phan et al. ............................ 606/148 |
| 6,017,358 | * | 1/2000 | Yoon et al. ........................... 606/205 |

* cited by examiner

*Primary Examiner*—Michael Buiz
*Assistant Examiner*—Vy Q Bui
(74) *Attorney, Agent, or Firm*—Blank Rome Comisky & McCauley LLP

(57) ABSTRACT

An instrument and method for suturing anatomical tissue with a suture needle includes a barrel having two needle holders therein which can be manipulated from a proximal end of the barrel to cause the needle to pass through tissue and to pass the needle from one needle holder to the other. The needle holders are operative to move the needle through a path in a plane not perpendicular to a longitudinal axis of the barrel. The angle of the plane with respect to the longitudinal axis can be adjusted.

18 Claims, 8 Drawing Sheets

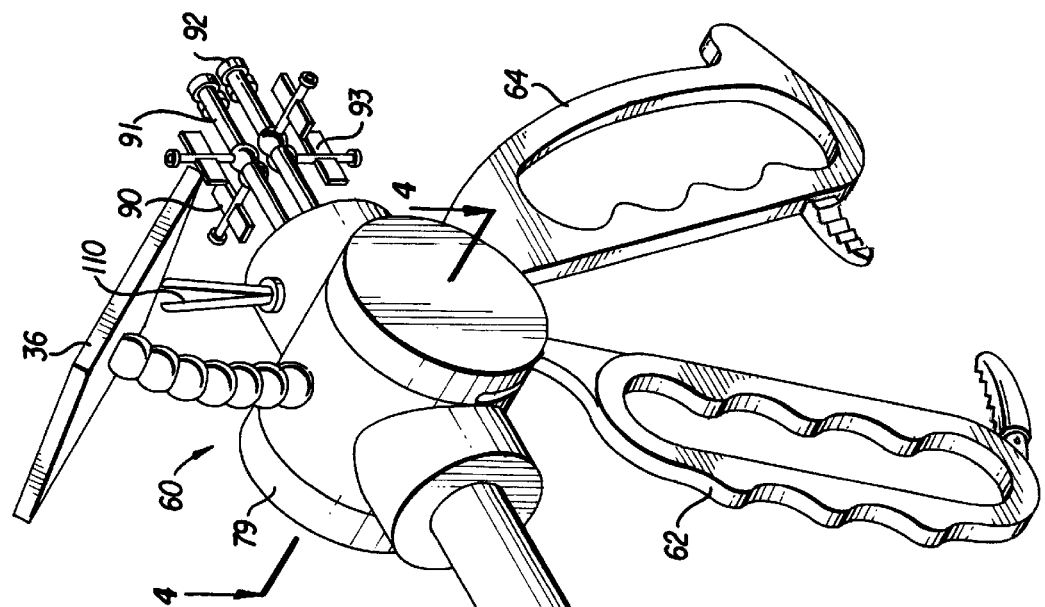
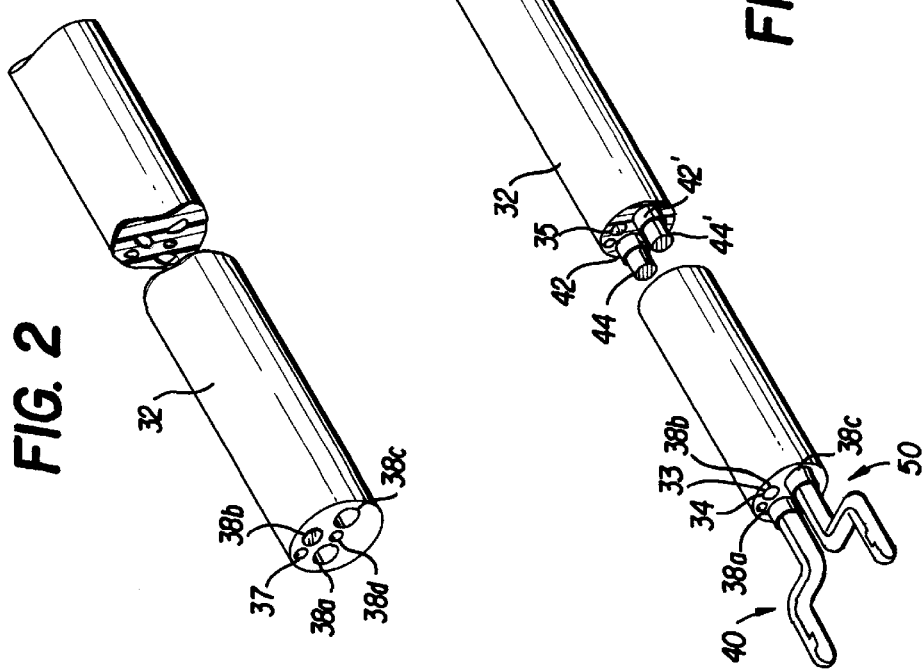

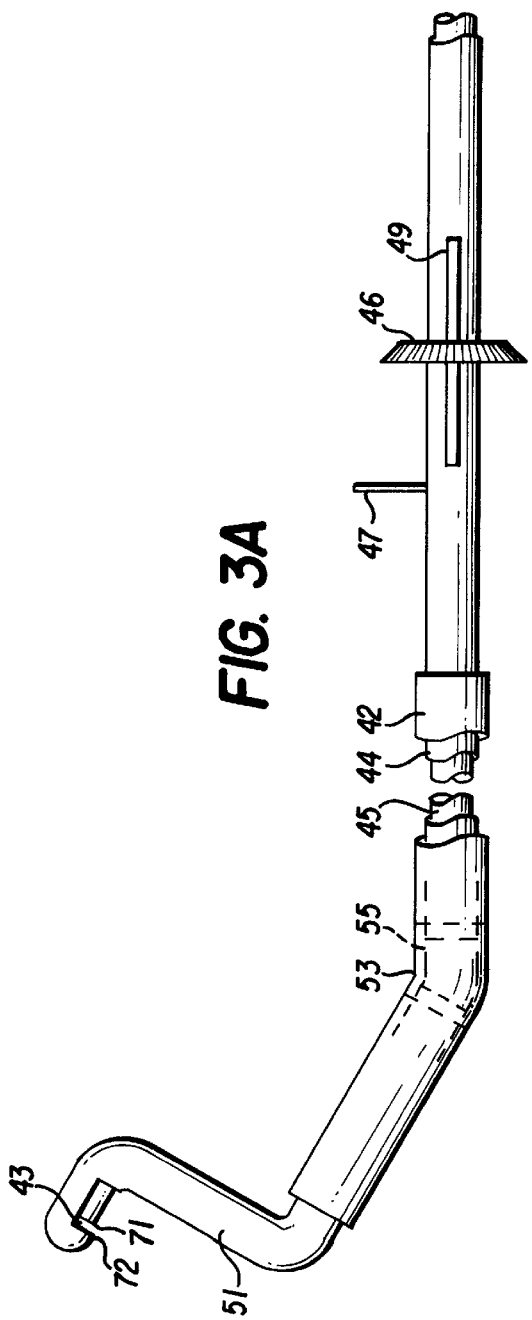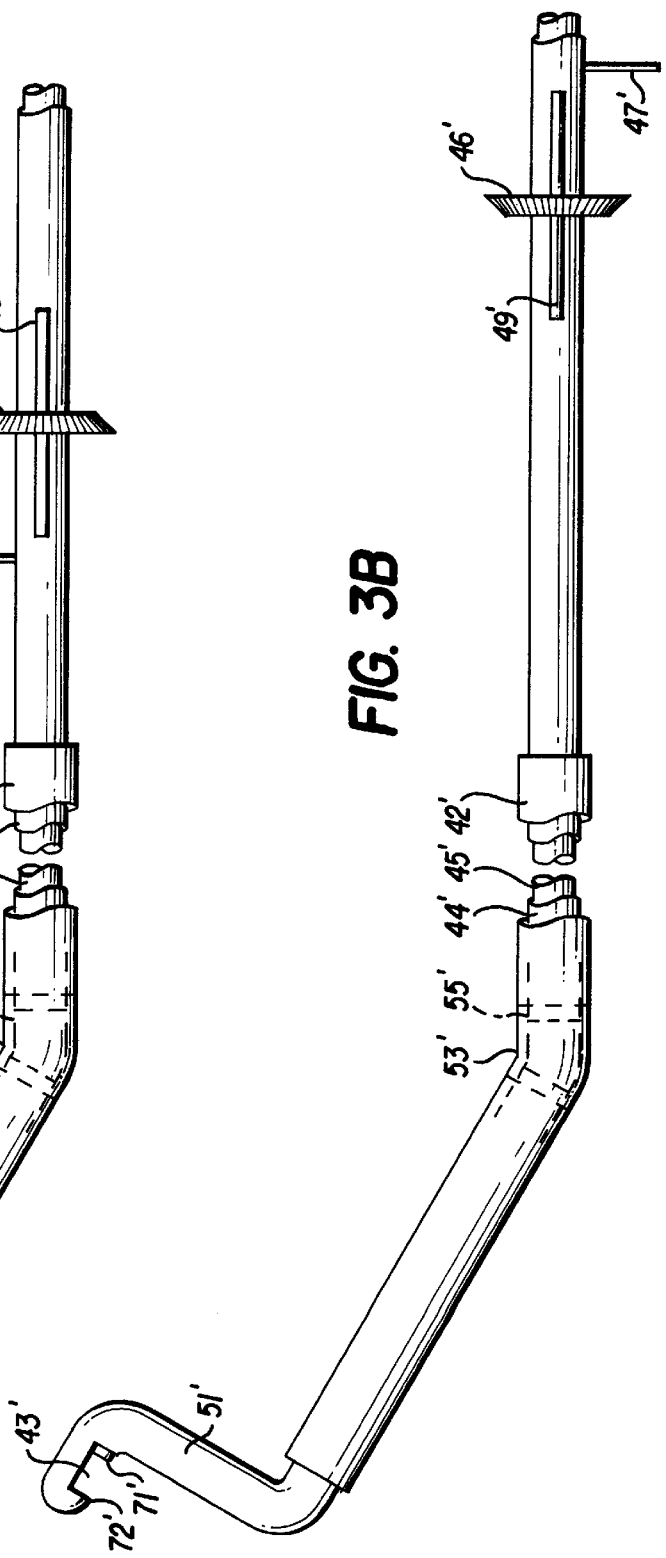

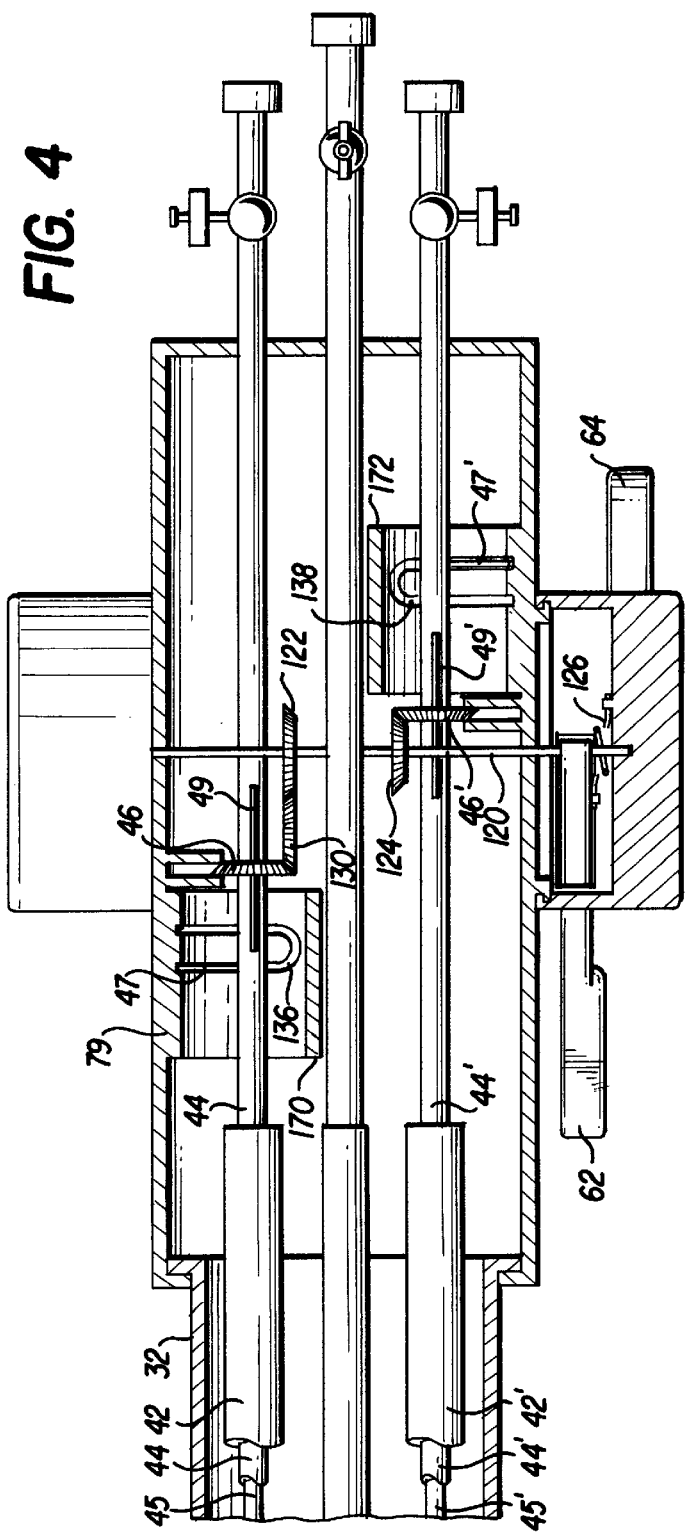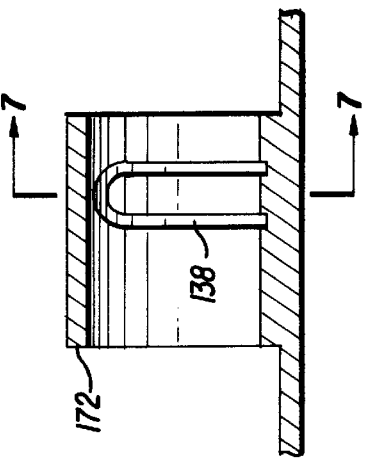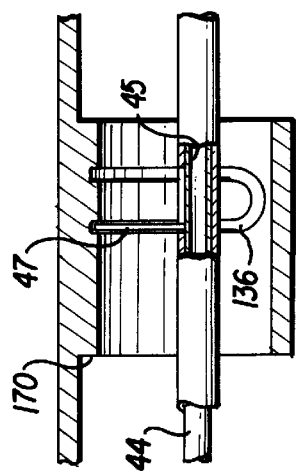

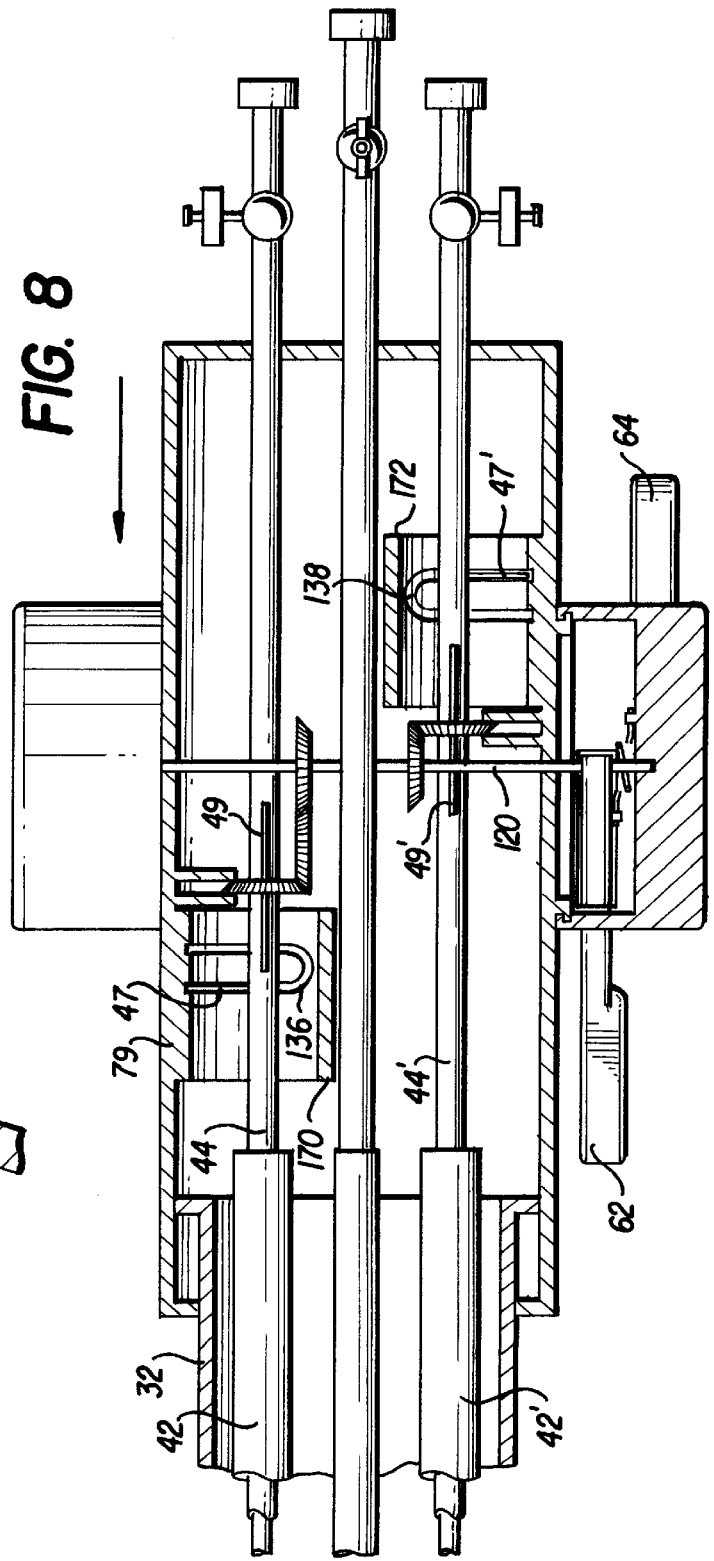

SUTURING INSTRUMENT WITH ANGLED NEEDLE HOLDER AND METHOD FOR USE THEREOF

RELATED PATENT APPLICATION DATA

This application claims priority from provisional application Ser. No. 60/089,659, filed on Jun. 17, 1998.

This application is related to applicant's applications Ser. No. 08/847,254, now U.S. Pat. No. 6,004,332—Ser. No. 08/847,252, now U.S. Pat. No. 6,080,180; Ser. No. 08/899,710; Ser. No. 08/847,189, now U.S. Pat. No. 6,017,358; Ser. No. 08/847,182, now U.S. Pat. No. 5,984,932; Ser. No. 905,215; Ser. No. 08/904,767, now U.S. Pat. No. 5,957,937; Ser. No. 08/902,311, now U.S. Pat. No. 5,954,731; Ser. No. 08/847,253; Ser. No. 08/877,764 now U.S. Pat. No. 5,993,466; and Ser. No. 08/904,764 now U.S. Pat. No. 5,993,467; the disclosures of which are incorporated herein by reference.

BACKGROUND OF THE INVENTION

1. Field of the Invention

The present invention pertains to suturing of bodily or anatomical tissue and, more particularly, to an instrument having a longitudinal axis and needle holders that extend at an angle to the longitudinal axis for passing a needle through a path that lies at an angle with respect to the longitudinal axis and a method for suturing using the instrument.

2. Description of the Related Art

Suturing of bodily tissue, that is, the practice of using lengths of suture material to ligate or approximate tissue, is a time consuming part of most surgical procedures including open surgery, microsurgery and minimally invasive surgery. "Open surgery" refers to surgery wherein the surgeon gains access to the surgical site by a relatively large incision and "minimally invasive surgery" refers to any type of surgery, such as laporoscopic surgery or "mini-lap" surgery, wherein the surgeon gains access to the surgical site via one or more portals or small incisions through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue one or more times, the surgeon ties a knot in the suture material. The knot tying procedure allows the surgeon to adjust the tension on the suture material to accommodate the particular tissue being sutured and to control approximation, occlusion, attachment or other conditions of the tissue.

The process of tissue penetration and tying a knot in the suture material can be time consuming and tedious work, particularly when performed in connection with microsurgery and minimally invasive surgery and can unduly prolong the duration of surgery and therefore the period in which the patient is under anesthesia. Nevertheless, minimally invasive surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating or replacing the suturing normally performed by use of a suture needle and a length of suture material. Alternative techniques proposed have included electrical coagulation, mechanical devices such as clips, clamps and staples, and lasers. However, no alternative technique has yet been well accepted by surgeons to produce the results obtained by suturing and knot tying. Thus, there is a great need for suturing instruments and techniques useful in minimally invasive and open surgery to permit surgeons to suture anatomical tissue and tie a knot in the suture material using suture needles and lengths of suture material in a time efficient, consistent and precise manner.

The performance of a minimally invasive procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments, having scissors, forceps, needle holders and the like into the anatomical cavity. The portal sleeve can be omitted and instruments can be inserted through a very small incision.

Suturing is typically performed with a needle holding instrument, or needle holder, having a pair of jaw members adapted to hold the body of a suture needle. The jaw members of the needle holding instrument are inserted into the cavity and are positioned at the operative site by manipulation of a handle at the proximal end of the instrument outside the body. With a suture needle held between the jaw members of the needle holding instrument, the handle is manipulated to cause a tip of the needle to be pushed through the tissue being sutured. Once the tip of the suture needle has been pushed through the tissue, the jaw members of the needle holding instrument must be opened to release the suture needle so that the tip of the needle can be grasped and pulled through the tissue therewith, or, after opening the jaw members, a second needle holding instrument must be introduced at the operative site through another portal to grasp the tip of the suture needle after it has emerged from the tissue being sutured.

The former technique requires difficult manipulation and further adjustment of the suture needle within the jaw members of the needle holder before another stitch can be made. While use of a second needle holding instrument for pulling the needle through the anatomical tissue allows the first needle holding instrument to grasp the body of the suture needle in the manner required to make additional stitches, a second puncture site is required to permit insertion of the second instrument. It is generally desirable to minimize the number of puncture sites created for performing a particular endoscopic procedure.

In minimally invasive procedures or other procedure in which the direction of access to the tissue to be sutured is limited, it is often difficult to suture using conventional instruments and techniques because the angle at which the instrument extends into the cavity is limited. For example, many procedures, such as bladder suspension and vaginal hysterectomy procedures, require suturing to be conducted at various angles. Therefore, it is difficult to accomplish these procedures without multiple puncture sites.

SUMMARY OF THE INVENTION

Accordingly, it is a primary object of the present invention to improve instruments and methods of suturing anatomical tissue.

It is a further object of the present invention to permit a suturing instrument as well as other instruments and devices to be introduced through a single portal or other opening in a minimally invasive procedure without having to withdraw the suturing instrument from the portal or other opening.

It is a further object of the invention to suture at an angle with respect to a longitudinal axis of a suturing instrument by passing a needle through a path that lies in a plane that is not perpendicular to a longitudinal axis of the suturing instrument to facilitate suturing in situations where the angle of approach to the tissue is limited.

The present invention allows suturing of anatomical tissue to be accomplished in a time efficient, consistent and precise manner. A first aspect of the present invention is generally characterized in an instrument for suturing anatomical tissue with a suture needle including a barrel, and at least one needle holder. The needle holder includes needle holding members, for example opposing jaws, movable relative to one another to permit a needle to be selectively grasped in the needle holder. When the needle holding members of the needle holder are operated to grasp the suture needle, the needle driver can be operated to drive the suture needle through anatomical tissue. The needle holder is constructed to pass the needle through a path that lies entirely in a plane that is not perpendicular to a longitudinal axis of the barrel. The angle between the plane and the longitudinal axis can be adjusted depending on the procedure.

Another aspect of the present invention is generally characterized in a method of suturing anatomical tissue using a length of suture material attached to a suture needle by passing a needle through a path that is not perpendicular to a longitudinal axis of the instrument with a needle driver. The method includes the steps of grasping the suture needle with needle holding members of the needle holder, positioning the anatomical tissue proximate a tip of the suture needle, moving the needle holder to cause the tip of the needle to penetrate the anatomical tissue releasing the needle from the needle holder.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

The invention is described through preferred embodiments and the attached drawing in which:

FIG. 1 is a perspective view of an instrument according to the invention;

FIG. 2 is a perspective view of the barrel of the instrument of FIG. 1;

FIG. 3A is a top view of the needle holder and the needle catcher removed from the barrel;

FIG. 3B is a top view of the needle holder and the needle catcher removed from the barrel;

FIG. 4 is a sectional view of a proximal end of the instrument of FIG. 1 taken along lien 4—4 of FIG. 1;

FIG. 5 is a detailed view in partial section of the cylindrical member and needle driver;

FIG. 6 is a detailed view of the other cylindrical member;

FIG. 7 is a sectional view of the cylindrical member taken along line 7—7 of FIG. 6;

FIG. 8 is a sectional view of the proximal end of the instrument of FIG. 1 with the needle holder and the needle catcher in the extended position;

DETAILED DESCRIPTION OF THE PREFERRED EMBODIMENTS

Figure 9:
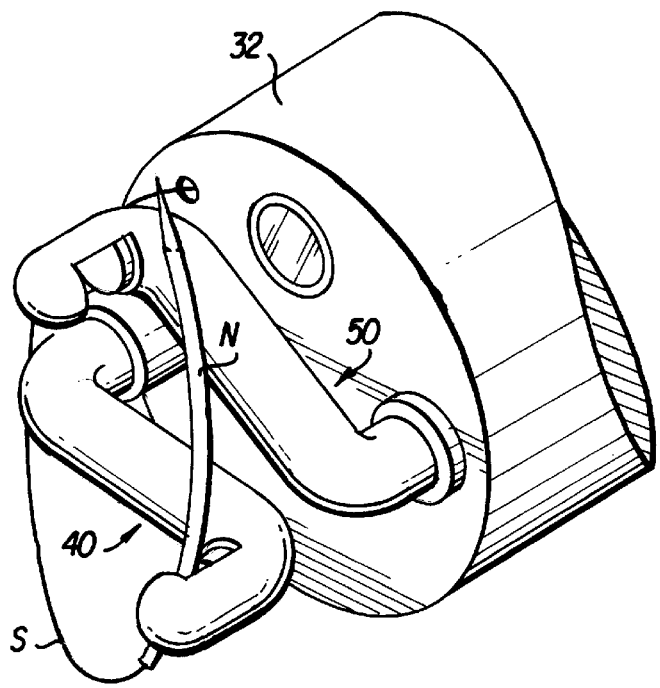
FIGS. 9–14 are perspective views of the distal end of the instrument of FIG. 1 illustrating a suturing process.

The suturing instrument of the present invention can be utilized to suture any type of anatomical tissue. Accordingly, while the instrument is described hereinafter for use in minimally invasive procedures, such as laparoscopy, the instrument can be used in open surgery and with catheters and other small and large diameter tubular or hollow cylindrical members providing access to small cavities, such as veins and arteries, as well as large cavities, such as the abdomen. The term "suturing" as defined herein refers to passing a needle through or around tissue one or more times while suture material is attached to the needle to pull the suture material through the tissue. The term "needle" as defined herein refers to any element having suture material attached thereto that can be passed through or around tissue.

A suturing instrument according to a first preferred embodiment of the present invention is illustrated at 30 in FIG. 1 and includes cylindrical barrel, or outer shaft 32, needle driver 40, and needle catcher 50. Needle driver 40 and needle catcher 50 are substantially contained within cylindrical barrel 32 as is described in detail below. The terms "needle driver" and "needle catcher" are used herein to describe, in terms of their function, elements that are structurally similar in the preferred embodiment. However, the function of these two elements is interchangeable. Also, these elements are sometimes referred to generically as "needle holders" herein. Needle driver 40 and needle catcher 50 can be moved proximally and distally in barrel 32 as will be described below.

As shown in FIG. 2, barrel 32 has operating channels 38a–d and suture material passage 37 extending longitudinally there through. Barrel 32 can have additional channels for receiving one or more additional instruments to be introduced in the abdominal cavity or barrel 32 can have fewer channels as needed. Optical fibers may extend through barrel 32 to transmit light from a proximal light source to the body cavity of a patient. Channels 38a–d can be defined by thin wall, tubular sleeves extending longitudinally through barrel 32 or by any other means.

FIG. 3A and FIG. 3B illustrate needle driver 40 and needle catcher 50 removed from barrel 32 for illustrative purposes. Needle driver 40 includes elongated, tubular outer member 42 and elongated tubular inner member 44 disposed within outer member 42. Inner member 44 defines a shaft that is rotatable in barrel 32. Holding member 45 extends through inner member 44, is flexible, and has abutment surface 71 that is disposed in notch 43 formed in inner member 44. Holding member 45 can be moved axially relative to inner member 44 to move abutment surface 71 from the closed position indicated by the solid line to the open position indicated by the dotted line as will be described in detail below.

Inner member (or, driver shaft) 44 is bent at a distal portion thereof to define arm 51. Outer member 42 includes bent portion 53 which is constructed of a shape memory material or the like. Therefore, a distal portion of the shaft, i.e. inner member 44 normally extends at an α angle (see FIG. 3) with respect to a longitudinal axis of barrel 32. The angle α is an inclination angle that the longitudinal axis makes with a rotation axis of the inner member 44. Preferably the angle is greater than 5° but can be adjusted based on the particular procedure. Inner member 44 includes bendable portion 55, constituted of a resilient material such as a spring, which corresponds in position to bent portion 53. In this manner, inner member 44 can assume a bent shape within outer member 42. For reasons which will become apparent below, bendable portion 55 is capable of transmitting rotation while flexing appropriately to conform to bent portion 53.

Holding member 45 is flexible but not substantially compressible and, as noted above, axially movable with respect to inner member 42. This permits the shank of a suture needle to be placed between abutment surface 71 and abutment surface 72 defined by notch 43 to be grasped thereby. Of course, abutment surfaces 71 and 72 can be shaped to correspond to the needle shank, or any other appropriate way, to firmly grasp and align the needle when holding member 45 is in the closed, or advanced, position.

Needle catcher 50 includes elongated, tubular outer member 42' and elongated tubular inner member 44' disposed within outer member 42'. Inner member 44' defines a shaft that is rotatable in barrel 32'. Holding member 45' extends through inner member 44', is flexible, and has abutment surface 71' that is disposed in notch 43' formed in inner member 44'. Holding member 45' can be moved axially relative to inner member 44' to move abutment surface 71' from the closed position indicated by the solid line to the open position indicated by the dotted line as will be described in detail below.

Inner member 44' is bent at a distal portion thereof to define arm 51'. Outer member 42' includes bent portion 53' which is constructed of a shape memory material or the like. Therefore, a distal portion of the shaft, i.e. inner member 44' normally extends at the angle α with respect to a longitudinal axis of barrel 32'. Inner member 44' includes bendable portion 55', constituted of a resilient material such as a spring, which corresponds in position to bent portion 53'. In this manner, inner member 44' can assume a bent shape within outer member 42'. For reasons which will become apparent below, bendable portion 55' is capable of transmitting rotation while flexing appropriately to conform to bent portion 53'. Holding member 45' is flexible and, as noted above, axially movable with respect to inner member 42'. This permits the shank of a suture needle to be placed between abutment surface 71' and abutment surface 72' defined by notch 43' to be grasped thereby. Of course, abutment surfaces 71' and 72' can be shaped to correspond to the needle shank, or any other appropriate way, to firmly grasp and align the needle when holding member 45' is in the closed position.

Needle driver 40 and needle catcher 50 can be of any configuration which permits selective grasping of the needle and relative motion between the needle driver and needle catcher, and can include needle holding members such as pivoting jaw members, slots and keepers, and moveable flanges. For example, the needle driver and needle catcher can have any of the configurations disclosed in the related applications noted above, the disclosures of which are incorporated herein by reference.

As illustrated in FIGS. 1 and 4, proximal controls 60 of the preferred embodiment include handles 62 and 64 extending out of housing 79 slidingly disposed on a proximal end of barrel 32. Handle 62 can be pivoted towards handle 64 to cause movement of the shafts of needle driver 40 and needle catcher 50 and holding members 45 and 45', in a coordinated manner as is discussed in detail below. Handle 62 is coupled to both needle driver 40 and needle catcher 50 in a manner which causes the desired rotation of the shafts of needle driver 40 and needle catcher 50 and the opening and closing operation of the respective holding members necessary for passing the needle between needle driver 40 and needle catcher 50 merely by squeezing and releasing handles 62 and 64 once or multiple times. The mechanism coupling handles 62 and 64 to needle driver 40 and needle catcher 50 can be designed to accomplish any stitching or tying function, such as that disclosed below, or any other appropriate motion. Such an automatic mechanism facilitates suturing by minimizing fatigue on the surgeon and reducing the possibility of operational errors.

FIGS. 4–6 illustrate an internal mechanism of proximal controls 60 in detail. Handle 64 is fixedly connected to housing 79. Handle 62 is movable and extends through a slot in housing 79 to be mounted on drive shaft 120 to cause drive shaft 120 to rotate when handle 62 is pivoted towards handle 64. Beveled gears 122 and 124 are also mounted on shaft 120 to rotate with shaft 120. Biasing member 126, shown as a coiled spring, biases handle 62 away from handle 64 to the illustrated position.

Beveled gears 122 and 124 are coupled respectively to beveled gears 46 and 46' that are mounted on outer member 42 and outer member 42' respectively. Note that beveled gears 46 and 46' are axially slidable with respect to outer members 42 and 42' respectively, but are fixed rotationally on the outer members by keys 49 and 49'. Beveled gear 124 is coupled directly to beveled gear 46' and beveled gear 122 is coupled to beveled gear 46 through beveled gear 130. Accordingly, rotation of drive shaft 120 causes inner member 44 to rotate in a first direction and causes inner member 44' to rotate in a second direction opposite to the first direction. The corresponding holding members are configured to rotate with the outer members.

Projection 47 extends from holding member 45. A free end of projection 47 slides in cam groove 136 formed in cylindrical member 170 fixed to housing 79. Similarly, projection 47' extends from holding member 45' and slides in cam groove 138 formed in cylindrical member 172. The cam grooves are shaped to cause the respective holding members to move axially, in distal and proximal directions, after the inner members rotate through a predetermined angle.

In operation, a needle is grasped between abutment surfaces 71 and 72 of needle driver 40 with proximal controls 60 in the position illustrated in FIG. 4. When the surgeon squeezes handle 62 towards handle 64, shaft 120 rotates to cause inner member 44 of needle driver 40 to rotate in a counter clockwise direction, as viewed from the distal end, and simultaneously to cause inner member 44' of needle catcher 50 to rotate in a clockwise direction, as viewed from the distal end. This results in the needle being pushed through tissue and into the jaws of needle holder 50 at which time cam grooves 136 and 138 cause holding members 45 and 45' to move relative to inner members 44 and 44' respectively in a manner to open needle driver 40 and close needle catcher 50. Specifically, as inner member 44 rotates counter-clockwise projection 47 enters the curved portion of cam groove 136 to cause holding member 45 to move proximally with respect to inner member 44. Similarly, the interaction between projection 47' and cam groove 138 causes holding member 45' to move distally and close around the needle. Note that the outer members are rotationally fixed in barrel 32 to maintain the desired angle of the distal ends thereof. Therefore, rotation of the inner members causes the needle to move through a path lying entirely in a predetermined plane P that is not perpendicular to the longitudinal axis of barrel 32 (see FIG. 1). Specifically, the predetermined plane P lies at the angle α at 90° with respect to the longitudinal axis of barrel 32.

Releasing handles 62 and 64 permits inner member 44 of needle holder 40 and inner member 44' of needle catcher 50 to rotate in opposite directions due to the force of biasing member 126 as projections 47 and 47' continue in the same direction through cam grooves 136 and 138. Now handles 62 and 64 can be compressed again to transfer the needle back to needle driver 40 for another stitch or for tying a knot in the manner described below with the appropriate holding members operating in a coordinated manner. Note that handles 62 and 64 are configured to be grasped while the surgeon's fingers pass through openings in the handles or while the surgeon's fingers are wrapped around outer portions of the handles to increase comfort and adaptability.

The shafts of needle driver 40 and needle catcher 50 (which shafts are constituted of the respective inner members) are disposed in channels 38a and 38c respectively to extend through barrel 32 and can be rotated about their respective longitudinal axes relative to barrel 32 in the manner described above. Operating channel 38d can be used as an operating channel for suction devices, irrigation devices, or any other appropriate instrument such as a cautery device or the like.

Suture material passage 37 extends to a proximal aperture (not illustrated) through which suture material S may be supplied from a spool or a container (not illustrated). A distal end of suture material S is attached to needle N and needle N is loaded in needle driver 40 between abutment surfaces 71 and 72. Suture material S can be inserted through suture material passage 37, prior to a suturing procedure, with a rigid guide tool or the like that is removed after a distal end of suture material S extends out of a distal end suture material passage 37.

In use, a distal end of suturing instrument 30 is inserted into a body cavity using known techniques. Note that the entire distal end can be inserted through a single puncture site. Prior to insertion, needle driver 40 and a needle catcher 50 are withdrawn axially in a proximal direction, by sliding housing 79 proximally with respect to barrel 32 to the position illustrated in FIG. 4, to draw bent portions 53 and 53' into barrel 32. In the withdrawn state, bent portions 53 and 53' are straightened out as illustrated in FIG. 9. Also, needle N which can be initially grasped by needle driver 40, can be disposed within the diametrical dimension of barrel 32 by positioning needle driver 40 and needle catcher 50 with arms 51 and 51' crossed also as illustrated in FIG. 9. This can be accomplished by selectively disengaging the needle holders form the automatic mechanism disclosed above and independently manipulating the needle holders as disclosed in the related applications incorporated herein by reference. Alternatively, arms 51 and 51' can be of a size which lies with the diametrical dimension of barrel 32, or arms 51 and 51' can be drawn into barrel 32 and straightened during insertion.

By grasping proximal controls 60, the distal end of suturing instrument 30 is guided to the operative site through a portal sleeve positioned in the wall of an anatomical cavity. The portal sleeve can be positioned in the anatomical cavity wall using any suitable penetrating technique, including those creating puncture sites by means of a removable obturator, such as a trocar, and can include a valve housing, if desired, to prevent loss of pneumoperitoneum during insertion and withdrawal of the instrument. Further, a retractable sheath can be provided to facilitate insertion through a portal sleeve valve by protecting distal ends of needle driver 40 and needle catcher 50. Visualization of the procedure can be accomplished using a conventional endoscope incorporated into channel 38b, for example (known as a single puncture procedure) or separately positioned within the anatomical cavity through a second portal sleeve located at another puncture site (known as a double puncture procedure).

Prior to insertion, needle N is securely held between abutment surfaces 71 and 72. Alternatively, needle N can be introduced into the body cavity by a separate instrument through a separate puncture sight or through an operating channel of instrument 30. In this embodiment, needle N is of a curved configuration. However, needle N can be straight or of any other appropriate shape. After insertion, a distal end of instrument 30 is guided to a position proximal tissue T, which is to be sutured. Once the distal end of instrument 30 is in the anatomical cavity, housing 79, and thus, needle driver 40 and needle catcher 50, is moved distally with respect to barrel 32 to the position of FIG. 8 to permit bent portions 53 and 53' to move out of barrel 32 and assume the normal bent position illustrated in FIGS. 1 and 10. With bent portions 53 and 53' in the normal bent position defining the angle α, rotation of inner members 42 and 42' will cause distal portions of needle driver 40 and needle catcher 50 to move through an arcuate path that is entirely in a plane that intersects a longitudinal axis of barrel 32 at angle α at 90° as indicated in FIG. 1. α is preferably greater than 5°. It will be seen from the description below that the angle of the extension of the distal portions of needle driver 40 and needle catcher 50 facilitate suturing tissue T which is offset at an angle from the longitudinal axis of barrel 32. For example, in vaginal hysterectomies and bladder suspension procedures, it is often necessary to suture at an angle with respect to the longitudinal axis of the barrel.

Figure 10:
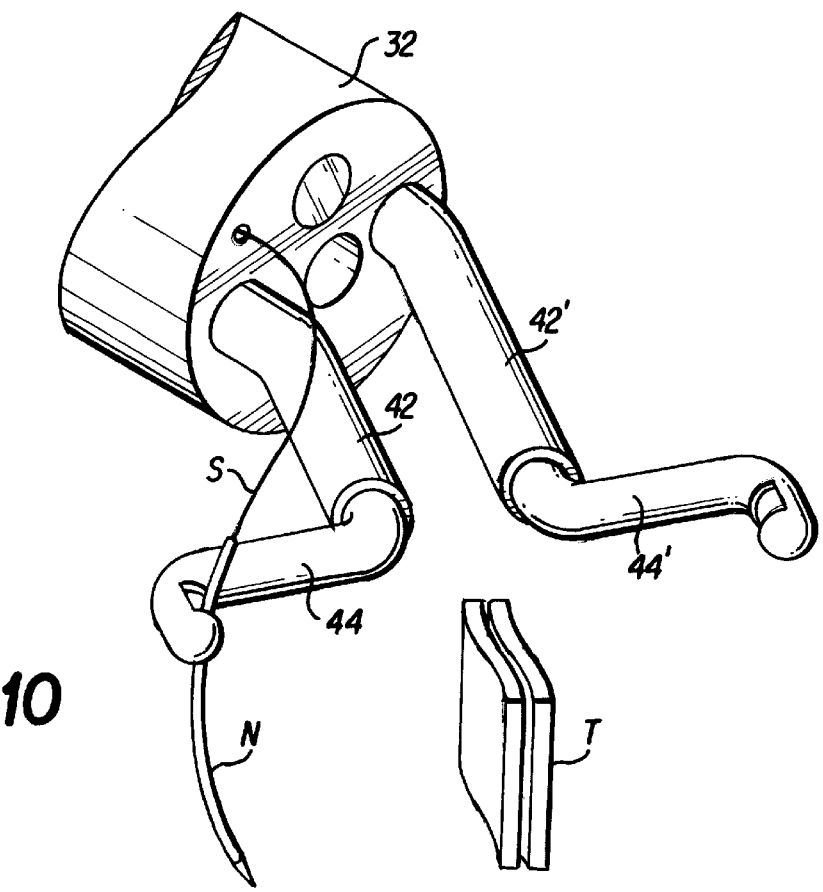
Figure 11:
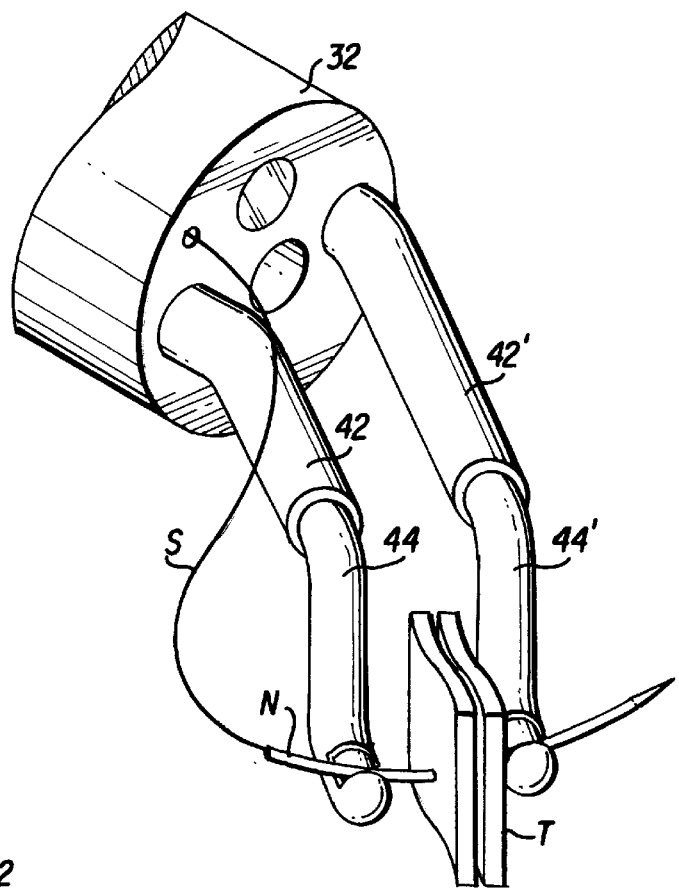

FIGS. 9–14, illustrate a suturing procedure after insertion of the distal end of instrument 30 into a body cavity. As illustrated in FIG. 9, needle N, having suture material S attached thereto, is grasped between abutment surfaces 71 and 72 of needle driver 40. The distal end of instrument 30 is then manipulated to place tissue T (to be sutured) between a tip of needle N and a distal portion of needle catcher 50, as shown in FIG. 10. Handle 62 is then pressed toward handle 64 to cause the shaft of needle holder apparatus 40 to be rotated in a counter-clockwise direction, as viewed in FIGS. 9–14 to cause a tip of needle N to penetrate and pass through a portion of tissue T as illustrated in FIG. 11. Simultaneously, a shaft of needle catcher 50 is rotated in a clockwise direction so that a tip of needle N is received between abutment surfaces 71' and 72'. Also, holding member 45 is moved proximally and holding member 45' is moved distally in the manner described above, to release needle N from needle driver 40 and grasp needle N with needle catcher 50.

Figure 12:
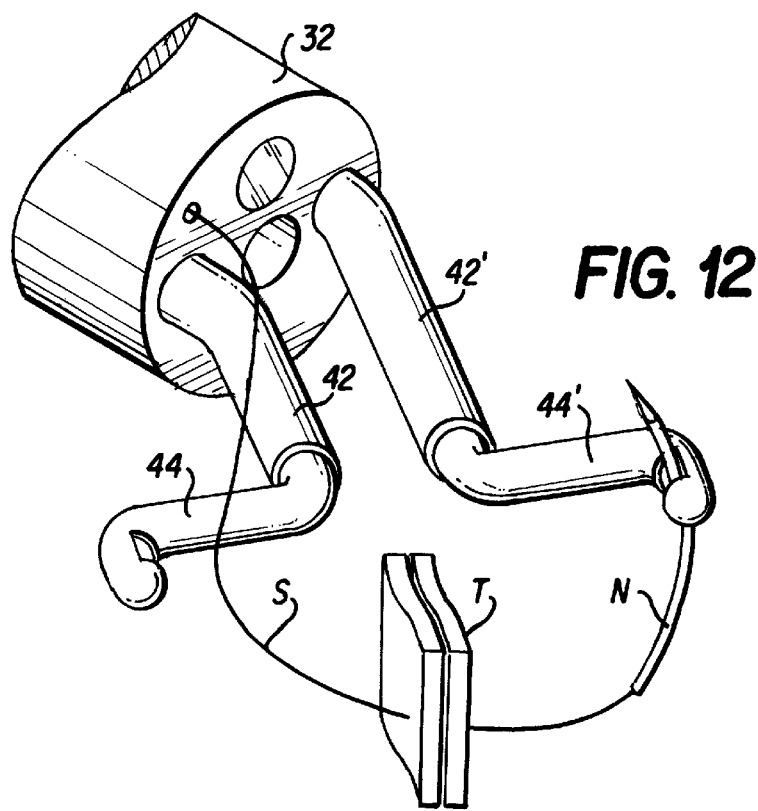
Figure 13:
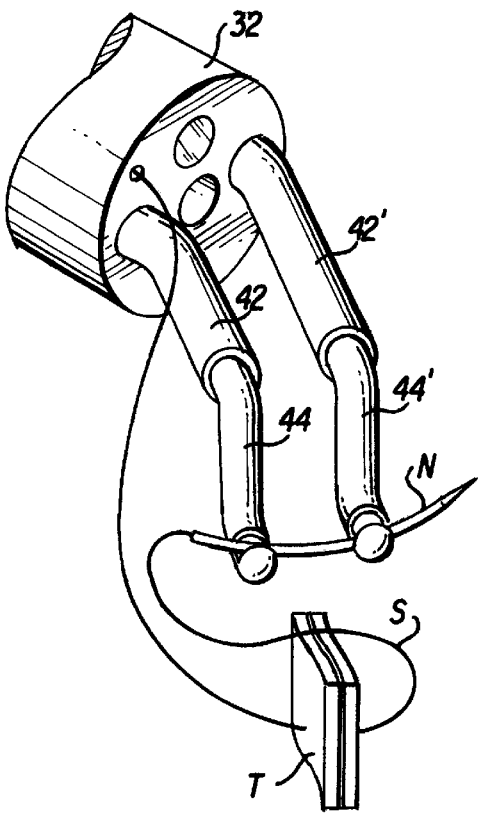
Figure 14:
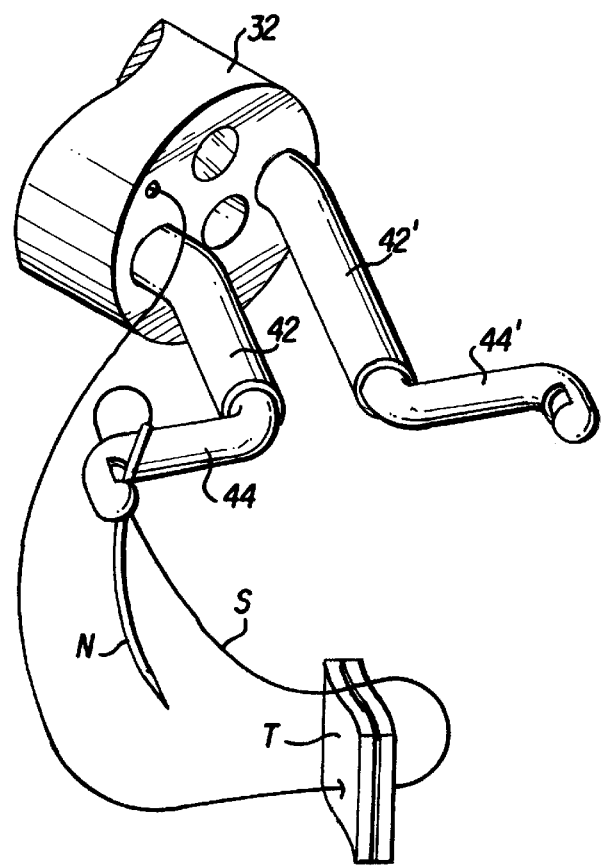

With needle N positioned in groove 43' of needle catcher 50 and grasped between abutment surfaces 71' and 72'. Handle 62 is then released from the compressed position to allow the shaft of needle catcher 50 to rotate in a counter-clockwise direction due to the biasing force on handle 62 and pull needle N, and thus suture material S attached to needle N, through tissue T, as illustrated in FIG. 12. Simultaneously, the shaft of needle driver 40 is rotated in a clockwise direction. As shown in FIG. 13 after needle N has been pulled through tissue T, the distal end of instrument 20 can then be moved away from tissue T (upwards in the drawing) and handle 62 can be pressed toward handle 64 again so that needle catcher 50 can be rotated clockwise and needle driver 40 is rotated counterclockwise to place needle N between abutment surfaces 71 and 72 once again and simultaneously needle N is grasped by needle driver 40, as shown in FIG. 13. Release of handle 62 will return instrument 30 to the position illustrated in FIG. 14. In this state a single stitch or "bite" has been made and instrument 30 is ready to make subsequent stitches in the manner discussed above, if needed. Of course, the suturing procedure can be conducted by manipulating needle driver 40 and needle catcher 50 in any appropriate manner, such as in the procedures disclosed in the related applications incorporated herein. Once the desired number of stitches have been made in the tissue, the surgeon can tie a knot in the suture material by manipulating needle driver 40 and needle catcher 50 or in any conventional manner. Cutting elements defined on the abutment surfaces can now be used to cut suture material S, by manipulating the appropriate needle holder, to permit withdrawal of instrument 30 and needle N.

Figure 15:
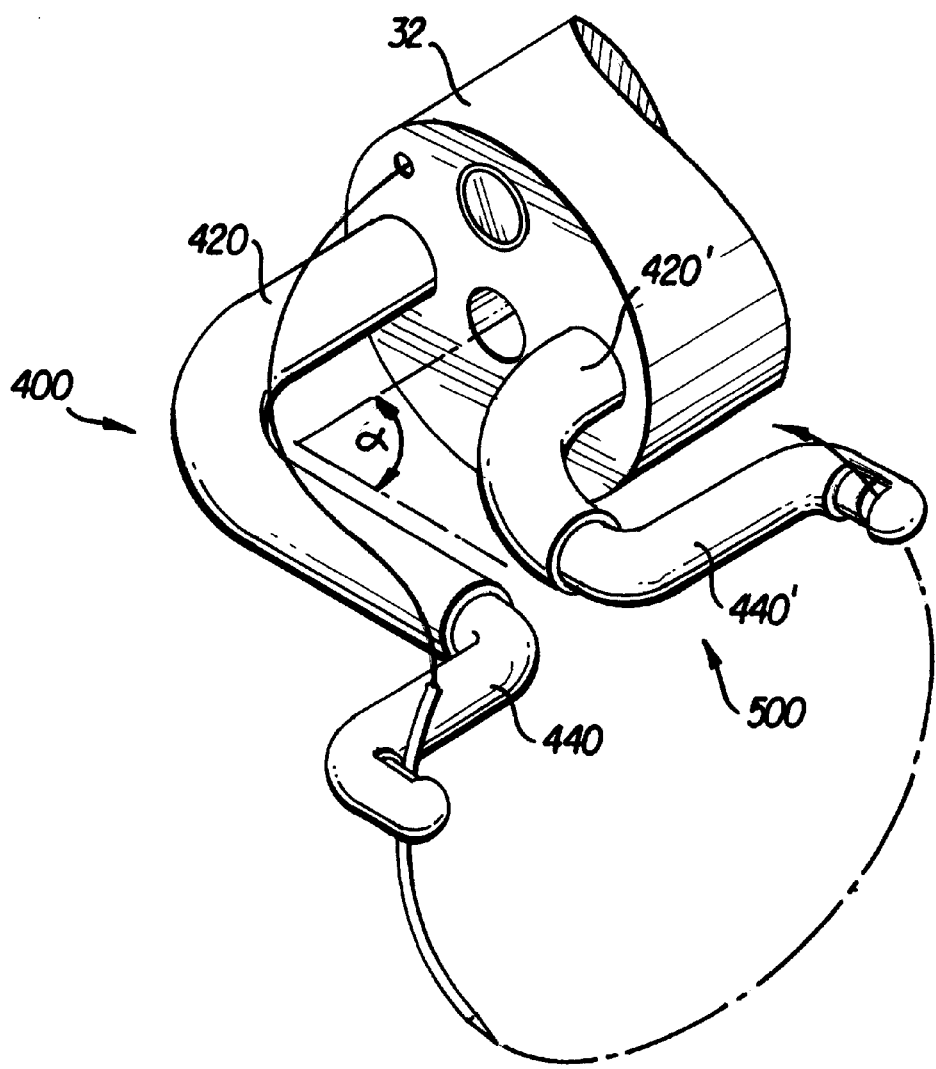
FIG. 15 is a perspective view of a distal end of another instrument according to the invention.

FIG. 15 illustrates the distal end of another instrument according to the invention. The instrument illustrated in FIG. 14 includes needle driver 400 having outer member 420 with a bent portion that defines an angle α of 90° in a natural state. Similarly, needle catcher 500 includes outer member 420 having a bent portion that defines an angle α of 90° in a natural state. The instrument illustrated in FIG. 15 permits suturing to be accomplished by moving the needle through a path entirely in a plane that extends in parallel to the longitudinal axis of barrel 32. The needle holders can be drawn into barrel 32 to straighten the bent portions in a manner similar to the instrument illustrated in FIG. 1. Further, the needle holders can be drawn into the instrument to varying degrees to adjust the amount of straightening of the bent portions and thereby adjust the angle α to be of a desired value. All other aspects of the instrument of FIG. 15 are similar to the instrument of FIG. 1. A procedure using the instrument of FIG. 14 can be viewed by an imaging device inserted through channel 38b or by a separate imaging device. If inserted through channel 38b, the imaging device can be steerable, or otherwise have a wide or variable viewing angle, to permit the suturing procedure to be viewed.

Note that needle N can be straight or curved. Also, suture material S can be connected to any portion of needle N and needle N can be stored in an operating channel prior to suturing. Further, a suturing motion can be accomplished by rotating barrel 32 in its entirety with the needle holders locked in position relative to barrel 32, with relative movement between needle driver 40 and needle catcher 50 only for passing needle N therebetween. The needle holders can be moved simultaneously, as described above, or in seriatim, i.e. one after the other. The needle holders are described above as being operated automatically in concert. However, independent controls can be provided for each needle holder and each needle holder can be manipulated individually.

At any point during the operative procedure, channel 38d can be used for irrigation or aspiration, can serve as a space for holding suture material S and/or needle N or as a portal for the introduction of other medical instruments such as, forceps, cutting members, ligators, or cautery devices. The holding members can be tubular to define operating channels through the needle holders for, aspiration, irrigation, the insertion of instruments, or the like. Proximal apertures 90–93 are provided for access to operating channels 38a–38d respectively. Needle driver 40 and needle catcher 50 can be modified to suture anatomical tissue with straight or slightly curved suture needles by shaping the abutment surfaces appropriately to receive and hold the needle.

From the above, it will be appreciated that the suturing instrument according to the present invention permits suturing of anatomical tissue during minimally invasive or open procedures without the need for multiple instruments inserted through multiple puncture sites. The needle driver and needle catcher each are movable and operable to grasp and release a suture needle N so that the suture needle can be driven through anatomical tissue. The angle of distal ends of the needle driver and needle catcher with respect to the barrel can be adjusted accordingly based on the particular procedure and angle of entry of the instrument. For example, the needle holders can be drawn into the barrel to varying degrees to adjust the angle.

The needle driver and the needle catcher, i.e. the needle holders, can be of the same design or of different designs as long as at least one is capable of grasping and releasing a needle. Also, the needle holders can be disposed in various portions of the barrel. For example, the instrument can have any of the configurations disclosed in the copending applications incorporated herein. The function of the needle driver and the needle catcher can be interchanged and suturing can be accomplished in the opposite direction depending on whether the surgeon is right-handed or left-handed or other practical considerations. The needle holders can have any configuration and can be movable in any manner to move the needle through the disclosed path. For example, the needle holders can move in 3 dimensions to accomplish the desired movement, can have hinged portions, bent portions or steerable portions. Also, the barrel can have a bent or bendable portion to achieve the desired angle.

One or more lengths of suture material can be attached to each suture needle at any desirable location along the body or tip of the needle including, but not limited to, the proximal end of the needle, intermediate or medial portions of the needle body, or locations adjacent the tip of the needle. It will also be appreciated that the instrument according to the present invention can be used with any type of standard suturing needle including, but not limited to, needles having sharp or blunt tissue penetrating tips, and needles having tissue penetrating tips at opposite axial ends of a needle body.

The holding mechanisms of the needle catcher and the needle driver shown and described herein are merely exemplary of the types of needle holding mechanisms that can be used according to the present invention. Accordingly, the needle holders can have any suitable configuration for cooperatively grasping needles to suture anatomical tissue including, but not limited to, configurations wherein holding members pivot, slide or otherwise move relative to one another to capture and release a needle. The holding members can, for example, be of straight, curved or angled configuration and can be provided with ribs, grooves, slots and/or holes along grasping surfaces to assure a positive grip. The holding members can also carry cutting members, such as slots with sharp edges or protruding blades, and can have opposed arcuate or concave portions for clamping tubular objects, such as organs, without compressing the objects. Also, only one, or more than two needle holders can be provided in the suturing and tying instrument as needed. Further, the needle holders can be configured to carry a needle in a longitudinal manner during insertion of the instrument and the needle can be turned transversely for suturing. Further, one of the needle catcher and needle driver can be fixed relative to the barrel.

The mechanisms for moving the needle catcher and needle driver relative to one another are merely exemplary of the types of mechanisms that can be used to perform these functions and other mechanisms can be used. The particular length and curvature of the suture needles shown and described herein as well as any angular displacements of the needle driver and catcher shown and described herein are merely exemplary, and it will be appreciated that other needle lengths and angular displacements can be used. The needle holders can move rotationally, arcuately, linearly, or through any appropriate path to accomplish suturing and knot tying.

One of the needle holders can be used as forceps, to grasp the tissue, during suturing or can contain a clip applicator. Therefore, the invention can be used for pickup and cutting, pickup and clipping, pickup and suturing, or lysis of adhesion procedures. Alternatively, a forceps device can be inserted through an operating channel. The needle holders can be used as unipolar or bipolar cautery electrodes by being electrically insulated from other portions of the instrument and being coupled to an electrical power source by connector 110. Further, tissue can be clamped between adjacent needle holders or tissue can be retracted by placing adjacent needle holders between tissue portions and moving the needle holders apart.

The components of the instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A suturing instrument for causing a needle having suture material attached thereto to pass through anatomical tissue, said instrument comprising:
    an elongated barrel having a longitudinal axis, a distal end, and a proximal end;
    a needle driver having a distal portion supporting a needle holding member and extending from said distal end of said barrel; and
    controls coupled to said needle driver and configured to manipulate said needle driver to cause the needle to move through a path in a predetermined plane not perpendicular or parallel to said longitudinal axis and thereby pass the needle through the anatomical tissue.

2. An instrument as recited in claim 1, further comprising a needle catcher having a needle holding member extending from said distal end of said barrel.

3. An instrument as recited in claim 2 wherein said needle driver comprises a driver shaft and said needle catcher comprises a catcher shaft, said controls including means for rotating said driver shaft and means for rotating said catcher shaft.

4. An instrument as recited in claim 3 wherein said driver shaft has a bendable portion which defines a distal end of said driver shaft extending at a first angle with respect to said longitudinal axis of said barrel and said catcher shaft has a bendable portion which defines a distal end of said catcher shaft extending at a second angle with respect to said longitudinal axis of said barrel.

5. An instrument as recited in claim 4, wherein said means for manipulating causes said distal end of said driver shaft and distal end of said catcher shaft to rotate about an axis that extends at said first angle and said second angle respectively.

6. An instrument as recited in claim 5, wherein said first angle and said second angle are substantially equal.

7. An instrument as recited in claim 6, wherein said first angle and said second angle are greater than 5°.

8. An instrument as recited in claim 1, comprising a rotation transmission mechanism rotating the needle driver about a driver rotation axis making an inclination angle α with the longitudinal axis of the elongated barrel of more than 0 degrees and less than 90 degrees.

9. An instrument as recited in claim 4, wherein said driver shaft and said catcher shaft are movable relative to said barrel from an extended position in which said bendable portions extend from a distal end of said barrel to a retracted position in which said bendable portions are contained within said barrel in a straightened state.

10. An instrument as recited in claim 7 wherein operating channels are defined through said barrel.

11. An instrument as recited in claim 4 further comprising a tubular first outer member in which said driver shaft is disposed and a tubular second outer member in which said catcher shaft is disposed and wherein said bendable portions are flexible and are maintained in a bent state by respective bent portions defined in said first and second outer members.

12. A method of suturing anatomical tissue using a length of suture material attached to a needle, said method comprising the steps of:
    introducing an instrument having a barrel into an area proximate the anatomical tissue;
    grasping the needle with a needle driver extending from the barrel; and
    positioning the anatomical tissue proximate a tip of the needle; and
    manipulating the needle driver to cause the needle to move through a path in a predetermined or parallel plane not perpendicular to a longitudinal axis of the barrel and to cause a tip of the needle to penetrate the anatomical tissue.

13. A method as recited in claim 12, further comprising the steps of:
    grasping the needle with a needle catcher extending from the barrel;
    releasing the needle from the needle driver; and
    manipulating the needle catcher to pull the needle entirely through the anatomical tissue.

14. A method as recited in claim 13 wherein said step of manipulating the needle catcher shaft comprises causing the needle to move through a path in the predetermined plane.

15. A method as recited in claim 14 wherein the needle driver comprises a driver shaft extending through at least a portion of the barrel, a bendable portion defined near a distal end of the driver shaft to cause the distal end of the driver shaft to extend at a first angle with respect to the longitudinal axis of the barrel, and a needle holding member disposed on the distal end of the driver shaft, the needle catcher comprising a catcher shaft extending through at least a portion of the barrel, a bendable portion defined near the distal end of the catcher shaft to cause the distal end of the catcher shaft to extend at a second angle with respect to the longitudinal axis of the barrel, and a needle holding member disposed on the distal end of the catcher.

16. A method as recited in claim 15, wherein the first angle and the second angle are greater than 5°.

17. A method as recited in claim 15 wherein the needle driver includes a tubular first outer member in which said driver shaft is disposed and a tubular second outer member in which the catcher shaft is disposed and wherein the bendable portions are flexible and are maintained in a bent state by respective bent portions defined in the first and second outer members.

18. A method as recited in claim 12, further comprising the step of adjusting the angle of the predetermined plane with respect to the longitudinal axis of the barrel based on the procedure.

* * * * *